United States Patent
North et al.

(10) Patent No.: US 6,599,891 B2
(45) Date of Patent: Jul. 29, 2003

(54) TREATMENT OF MACULAR EDEMA

(75) Inventors: Janice North, Vancouver (CA); Peter Hnik, Vancouver (CA); H. Andrew Strong, North Vancouver (CA)

(73) Assignee: QLT Inc., British Columbia (CA)

(*) Notice: Subject to any disclaimer, the term of this patent is extended or adjusted under 35 U.S.C. 154(b) by 0 days.

(21) Appl. No.: 10/199,662

(22) Filed: Jul. 19, 2002

(65) Prior Publication Data

US 2003/0099596 A1 May 29, 2003

Related U.S. Application Data

(60) Provisional application No. 60/329,009, filed on Oct. 12, 2001, and provisional application No. 60/306,731, filed on Jul. 20, 2001.

(51) Int. Cl.$^7$ .......................... A61K 31/33; A61H 5/00
(52) U.S. Cl. ........................................ 514/183; 601/15
(58) Field of Search ............................ 514/183; 601/15

(56) References Cited

U.S. PATENT DOCUMENTS 5,756,541 A * 5/1998 Strong et al. ............... 514/502
5,798,349 A * 8/1998 Levy et al. ................. 514/185
6,270,749 B1 * 8/2001 Blumenkranz et al. .... 424/9.61

FOREIGN PATENT DOCUMENTS

WO   WO 02/064163   8/2002

OTHER PUBLICATIONS

Treatment of Age–related Macular Degeneration with Photodynamic Therapy (TAP) Study Group, "Photodynamic Therapy of Subfoveal Choroidal Neovascularization in Age–Related Macular Degeneration with Verteporfin: One–Year Results of 2 Randomized Clinical Trials–TAP Report 1" Archives of Ophthalmology 117(10):1329–1345 (1999).

Boyer, D.S., et al., "Efficacy of Verteporfin Photodynamic Therapy on Laser Induced Choroidal Neovascularization and the Ancillary Effect on Diabetic Microvasculopathy" IOVS, Meeting Info: Annual Meeting of the Association for Research in Vision and Ophthalmology Fort Lauderdale, Florida, Apr. 29–May 4, 2001 42(4):S695 (2001).

Lovestam–Adrian, M., et al., "Photocoagulation of Diabetic Macular Oedema: Complications and Visual Outcome" Acta Ophthalmologica Scandinavica 78(6):667–671 (2000).

Aiello, L. M., et al., "Diabetic Retinopathy" Chapter 26 In *Retina–Vitreous–Macula: Diabetic Retinopathy* (Guyer et al., eds.) W.B. Saunders Co. pp. 316–344 (1999).

Early Treatment Diabetic Retinopathy Study Research Group, "Photocoagulation for Diabetic Macular Edema: Early Treatment Diabetic Retinopathy Study Report Number 1" Arch Opthalmol 103:1796–1806 (1985).

Early Treatment Diabetic Retinopathy Study Research Group, "Early Photocoagulation for Diabetic Retinopathy: ETDRS Report Number 9" Ophthalmology 98:766–785 (1991).

Ferris, F. L. and Davis, M. D., "Treating 20/20 Eyes with Diabetic Macular Edema" Arch Ophthalmol 117(5):675–676 (1999).

Ferris, F. L. and Patz, A., "Macular Edema. A Complication of Diabetic Retinopathy" Surv Ophthalmol 28(Suppl):452–461 (1984).

Klein, R., et al., "The Wisconsin Epidemiologic Study of Diabetic Retinopathy: XI. The Incidence of Macular Edema" Opthalmology 96:1501–1510 (1989).

* cited by examiner

Primary Examiner—Ramond Henley, III
(74) Attorney, Agent, or Firm—Morrison & Foerster LLP

(57) ABSTRACT

The invention relates to the use of photodynamic therapy (PDT) to treat macular edemas, including DME, CRVO and BRVO. It provides an alternative to photocoagulation and the disadvantages associated therewith.

31 Claims, No Drawings

TREATMENT OF MACULAR EDEMA

RELATED APPLICATIONS

This application claims benefit of priority from U.S. Provisional Applications No. 60/306,731, filed Jul. 20, 2001, and No. 60/329,009, filed Oct. 12, 2001, which are hereby incorporated in their entireties as if fully set forth.

TECHNICAL FIELD

The invention relates to the use of photodynamic therapy (PDT) in the treatment of macular edema of various etiologies, such as DME and macular edema due to central vein occlusion (CRVO) or branch retinal vein occlusion (BRVO).

BACKGROUND OF THE INVENTION

Macular edema refers to the occurrence of edema in the macula, a region in the center of the retina involved in acute and detailed vision. Edema refers to the presence of excess interstitial fluid (or fluid in spaces between cells) in tissues. Thus the presence of excess fluid or increases in interstitial fluid pressure that increase fluid volume can result in edema.

The more severe and visually threatening forms of macular edema have been termed "clinically significant macular edema", as explained below. Clinically significant macular edema (CSME) occurs most frequently in type II DM requiring insulin (11%), less in type II without insulin (4%) and in type I (6%). Clinically significant macular edema may appear at any stage of DR (Klein, R. et al. *Ophthalmology* 1989, 96: 1501–1510.). The Early Treatment Diabetic Retinopathy Study (ETDRS) defined CSME as 1.) Retinal thickening involving, or within 500 μm from, the center of the macula; 2.) Hard exudate(s) (with thickening of the adjacent retina) at or within 500 μm from the center of the macula; and 3.) A zone of retinal thickening one disc area or larger in size, any part of which is within one disc diameter from the center of the macula (Arch Ophthalmol 1985, 103: 1796–1806.).

Diabetic retinopathy (DR) is a long-term consequence of diabetes mellitus (DM) that can lead to significant vision loss. It is characterized by microaneurysms, excessive vascular permeability, and areas of retinal non-perfusion and retinal neovascularization. Diabetic macular edema (DME) is the principal mechanism of vision loss in non-proliferative diabetic retinopathy and occurs primarily as the result of macular exudation. This may occur either as the result of focal leakage of exudate from one or more clusters of microaneurysms and dilated capillaries, each often surrounded by a ring of yellow, deep retinal exudates, or as a result of diffuse leakage from most of the retinal vasculature in the macular area. In general, the loss of central vision parallels the degree of intraretinal exudate. Over one-half of diabetics with macular edema will lose two or more lines of visual acuity within two years (Ferris, F. L. and Patz, A. *Surv Ophthalmol* 1984, May; 28 Suppl: 452–461). These patients are very common in most retina practices and the disease represents a significant public health problem.

Following diabetic retinopathy, retinal venous occlusive disease is the most common retinal vascular disorder. Central retinal vein occlusion (CRVO) is a common retinal vascular disorder with potentially blinding complications. It can be ischemic or nonischemic. Men are more commonly affected than women, age at presentation is usually in the low to mid 60s. Associated risk factors are history of systemic hypertension, cardiovascular disease, diabetes mellitus, blood hyperviscosity, glaucoma, hyperopia and others. The condition is characterized by intraretinal hemorrhages in all four quadrants, dilated and torturous retinal venules, optic disc edema and retinal edema (including macular edema).

Macular edema is common in most central retinal vein occlusions and accounts for loss of visual acuity in many eyes. A recent, large, multicenter clinical trial was conducted to assess the efficacy of grid photocoagulation for macular edema in CRVO. The treatment did reduce angiographic evidence of macular edema but visual acuity results were not significantly different in the treated and untreated group. Therefore, the Central Vein Occlusion Study does not recommend laser photocoagulation for treatment of macular edema.

Another cause of macular edema is branch retinal vein occlusion (BRVO). BRVO is caused by an obstruction of one or more than one of the branch retinal veins in the retina. There is no sex predilection and the condition is most frequent at the 7th decade of life. Associated risk factors are history of systemic hypertension, cardiovascular disease, glaucoma, increased body mass index at the age of 20 years, higher levels of alpha-2-globulin, and eyes with shorter axial lengths. The acute phase is characterized by segmental (based on the location of the occluded vein) intraretinal hemorrhage.

Beyond DME, CRVO and BRVO, the occurrence of postoperative cystoids, ocular tumors, intraocular inflammation, wet AMD, light toxicity, and retinitis pigmentosa may lead to macular edema. The occurrence of these conditions do not, however, indicate a necessary presence of macular edema. Macular edema may also be drug induced.

Currently the therapy shown to be even partially effective at reducing the rate of vision loss in patients that have macular edema is photocoagulation. However, laser photocoagulation results in significant visual improvement in only a limited number of cases. Conclusions from the ETDRS (Ophthalmology 1991, 98:766–785) indicate that eyes with mild to moderate nonproliferative diabetic retinopathy and clinically significant macular edema, when treated with focal argon blue-green or argon green laser to microaneurysms and a grid treatment to zones of diffuse leakage and non-perfusion, show the maximum benefit of treatment. However, there appears to be little to gain from early photocoagulation in eyes where edema does not involve the center of the macula and only moderate gain, when it does (Guyer, D. R. et al. Retina—Vitreous—Macula: Diabetic Retinopathy; W. B. Saunders company. 1999, 316–344). In eyes with mild to moderate macular edema, panretinal photocoagulation is not recommended.

Although laser treatment is somewhat effective at reducing the rate of vision loss it is also a destructive treatment with unwanted side effects that can cause loss of central visual acuity and scotoma formation (Ferris, F. L. Arch Ophthalmol 1999, 117(5): 675–676). Patients with visual acuity of 20/20 or better are less likely to recognize the benefits from this aggressive treatment and more likely to notice its side effects, that can include some loss of peripheral vision, and a reduction in color and night vision. Patients often have difficulty in accepting treatment with laser photocoagulation, knowing that they potentially are going to lose some of their vision and day to day tasks such as reading and driving will be much harder to perform. In general photocoagulation is considered a less than satisfactory therapeutic regimen for the treatment of macular edema.

Photodynamic therapy is a two-step process consisting of an intravenous injection of a photosensitizer (light-activated drug) followed by the application of light of an appropriate wavelength that is absorbed by the photosensitizer. The light sources most commonly used are non-thermal lasers or light emitting diodes (LEDs). Photosensitizers accumulate in target tissues preferentially, including vascular endothelial cells and tumor cells. In combination with localized light administration, this allows for selective treatment of the pathologic tissue. After exposure to light at a wavelength absorbed by the photosensitizer, an energy transfer cascade is initiated, culminating in the formation of singlet oxygen which generates intracellular free radicals. These free radicals can disrupt cellular structures such as the cell membrane, mitochondria, and lysosomal membranes. Photodynamic therapy has been suggested for the treatment of a wide variety of medical conditions, including cancer, autoimmunity, inflammation, cardiovascular disease, infection with pathogens, and conditions resulting from unwanted neovasculature.

Citation of documents herein is not intended as an admission that any is pertinent prior art. All statements as to the date or representation as to the contents of documents is based on the information available to the applicant and does not constitute any admission as to the correctness of the dates or contents of the documents.

DISCLOSURE OF THE INVENTION

The present invention provides photodynamic therapy (PDT) as a treatment for macular edema that is more effective and less damaging to the tissue surrounding an edematous lesion than laser photocoagulation. In one embodiment of the invention, the treatment is directed to the macula, even if the underlying cause or etiology of the macular edema is located elsewhere.

In other embodiments, the invention provides methods for the treatment of DME or macular edema resulting from central retinal vein occlusion (CRVO) or branch retinal vein occlusion (BRVO). CVRO is caused by an obstruction of the central retinal vein at the level of lamina cribrosa by compression of the sclerotic retinal artery, hemodynamic disturbances leading to thrombus formation, degenerative or inflammatory disease within the vein. BRVO is caused by an obstruction of one or more than one of the branch retinal veins in the retina. The invention provides a treatment for any macular edema (ME), including but not limited to those associated with diabetes, CRVO or BRVO (including ischemic or nonischemic forms), by use of PDT.

Thus in one aspect, the invention provides means to reduce or reverse ME or its effects due to leakage of exudate from an lesion, associated with diabetes, CRVO or BRVO or other similar type of lesion, in an eye of an animal, comprising the steps of identifying said lesion in the eye of the animal, administering to the animal an amount of a photosensitive compound sufficient to allow said photosensitive compound to localize in said lesion, permitting sufficient time to elapse to allow said photosensitizer to localize in said lesion, and irradiating said lesion with an amount of radiation having one or more than one wavelength absorbed by the photosensitive compound. In another aspect, and to the extent that some or all of the ME lesions may not be present in the macula, the invention provides PDT directed to the macula to treat the macular edema. The invention may, of course treat both eyes, if afflicted with ME, of a single animal.

The invention also provides a method for the reduction of interstitial fluid volume and/or pressure in the eye of a subject having ME by use of PDT comprising administration of a photosensitive compound and irradiating the macula of said subject with radiation containing one or more than one wavelength absorbed by said compound.

In a further aspect of the invention, ME resulting from a condition without a lesion in the macula may be treated by PDT directed at the macula. For example, and without limiting the invention, the invention also provides means to reduce or reverse ME due to CRVO or BRVO by directing PDT to the macula and not to the site of the occlusion.

In preferred embodiments of the invention, the photosensitive compound is a green porphyrin, most preferably verteporfin. In another preferred embodiment, light is administered from a laser at a dosage of between about 1 and about 50 J/cm$^2$, and more preferably between about 5 and about 35 J/cm$^2$. Other preferred dosages include between about 1 and about 5 J/cm$^2$, about 5 and about 10 J/cm$^2$, about 10 and about 15 J/cm$^2$, about 15 and about 20 J/cm$^2$, about 20 and about 25 J/cm$^2$, about 25 and about 30 J/cm$^2$, about 30 and about 35 J/cm$^2$, about 35 and about 40 J/cm$^2$, about 40 and about 45 J/cm$^2$, and about 45 and about 50 J/cm$^2$. Most preferred dosages are between 1 and 50 J/cm$^2$, 5 and 35 J/cm$^2$, and 10 and 20 J/cm$^2$.

In another preferred embodiment, the animal is a human (male or female) patient afflicted or diagnosed with DME or macular edema due to CRVO or BRVO. In one embodiment of the invention in relation to DME, the edematous lesions are focal in nature (resulting in focal leakage). In a preferred embodiment, the DME edematous lesions are diffuse in nature (resulting in diffuse leakage).

In another aspect, the invention is directed to a method of reducing or preventing loss of visual acuity or vision loss in a patient with ME, comprising the steps of administering an effective amount of a photosensitive compound to a patient, waiting for a sufficient period of time for the photosensitive compound to localize in the lesion and/or macula, and irradiating the lesion and/or macula with an effective or sufficient amount of light having a wavelength absorbed by the photosensitive compound sufficient to reduce or prevent loss of visual acuity (correctable by the use of lenses) or vision loss (which is not correctable by the use of lenses). Such methods may be applied to patients afflicted with DME or macular edema due to CRVO or BRVO.

PDT treatment may provide a better overall visual outcome than laser photocoagulation for the treatment of macular edema because there may be less indiscriminate mass destruction of normal tissues with PDT. This may be especially true in cases of diffuse DME lesions or macular edema due to CRVO or BRVO, which are less amenable to treatment with photocoagulation than focal lesions.

MODES OF CARRYING OUT THE INVENTION

The use of PDT for the treatment of neovasculature in the eye is well known. In particular, the use of PDT with verteporfin (also known as BPD-MA) for the treatment of subfoveal choroidal neovascularization in age-related macular degeneration. The use of PDT in the treatment of macular edema, in which the pathology is primarily not due to the proliferation of new vessels (neovascularization), but due to a large number of other possible causes, has not been suggested or disclosed. Possible causes of macular edema include the occurrence of postoperative cystoids, ocular tumors, intraocular inflammation, wet AMD, light toxicity, and retinitis pigmentosa. Macular edema may also be drug induced.

Without being bound by theory, and offered to assist with the understanding of the invention, macular edema may be the result of vascular instability and/or chronic inflammation, especially within the eye or ocular tissues, and may be treated by PDT to the macula, even if the underlying etiology is specifically or generally located elsewhere. The invention provides PDT methods which include the administration of a photosensitizer (PS) and irradiation with a wavelength of electromagnetic radiation capable of activating the PS.

Preferred PSs for use in the invention are the green porphyrins, and preferred irradiation is with visible light. A particularly preferred PS is a lipid formulation of benzoporphyrin derivative monoacid ring A, which is also known as verteporfin or BPD-MA. Following, or simultaneous with, delivery of the PS, irradiation may be performed by any radiation source. Examples of sources of visible light radiation include operating room lamps, halogen lamps, fluorescent lamps, laser light sources, and combinations thereof. Additional examples of light sources include light emitting diode (LED) panels.

In the case of green porphyrins, preferably, radiation such as 690 nm light in the case of BPD-MA use. In the practice of the invention, radiation is delivered to the macula or the site of a lesion such as that of DME or other specific lesion that results in macular edema. Without limiting the invention, such administration may be light administration through the eye from an external source. In one embodiment, the light is from a laser, such as that capable of stably delivering 689+/−3 nm, and delivered to the site of the macula, a specific location therein, or the site of an underlying DME or other lesion resulting in macular edema.

Administration of the PS may be by delivery using any appropriate means including, but not limited to, systemic, local, or even direct application to the target tissue. Local delivery of the PS provides a high local concentration while reducing the likelihood of transient skin photosensitivity or other undesirable side effects that may follow systemic PS administration. The photodynamic therapy (PDT) according to the invention can be performed using any of a number of photoactive compounds (or photosensitizers). For example, various derivatives of hematoporphyrin have been described, including improvements on hematoporphyrin derivative per se such as those described in U.S. Pat. Nos. 5,028,621; 4,866,168; 4,649,151; and 5,438,071. In addition, pheophorbides are described in U.S. Pat. Nos. 5,198,460; 5,002,962; and 5,093,349; bacteriochlorins in U.S. Pat. Nos. 5,171,741 and 5,173,504; dimers and trimers of hematoporphyrins in U.S. Pat. Nos. 4,968,715 and 5,190,966. In addition, U.S. Pat. No. 5,079,262 describes the use of a precursor to hematoporphyrin, aminolevulinic acid (ALA), as the source of a photoactive compound. The use of phthalocyanine photosensitive compounds in photodynamic therapy is described in U.S. Pat. No. 5,166,197. Other possible photoactive compounds include purpurins (such as tin-ethyl etiopurpurin), merocyanines, iminochlorinaspartic acid derivative (U.S. Pat. No. 6,063,777), texaphyrins (such as motexafin lutetium) and porphycenes. The contents of all of the foregoing patents are incorporated herein by reference as if fully set forth.

Particular preferred photoactive compounds for use in the invention method are green porphyrins. These porphyrins are described in U.S. Pat. Nos. 4,883,790; 4,920, 143; 5,095,030; and 5,171,749, the entire contents of which are incorporated herein by reference. As these photoactive agents represent a particularly preferred embodiment, exemplary formulas for these compounds are represented below.

Additional suitable PSs for the practice of the invention are of a wide variety, including, without limitation, porphyrin related compounds such as hematoporphyrin derivative, Photofrin® (Axcan Pharmaceuticals) porfimer sodium, the green porphyrins such as the BPDs, purpurins, chlorins, fluorins, etiopurpurins, and the like as well as phthalocyanines, pheophorbides, deuteroporphyrins, texaphrins, and the like.

Examples of these and other PSs for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl(3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11), 22-ergostatetraene-3 β-o1, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391–475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethylethyl)]-; pyrilium perchlorate, 2,6-bis(1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl-ethyl)-4-[1-[2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-pentenyl)]-; telluropyrilium tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl) bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethyl-ester; porphine-2,18-dipropanoic acid, 7-[2-dimethyl-amino)-2-oxoethyl]-8-ethylidene-8-ethyl-7,8-dihydro-3,7, 12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl)chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl)coumarin; 6-methylcoumarin; 2H-selenolo[3,2-g][1]benzopyran-2-one; 2H-selenolo[3,2-g][1]benzothiopyran-2-one; 7H-selenolo[3,2-g][1]benzoseleno-pyran-7-one; 7H-selenopyrano[3,2-f][1]benzofuran-7-one; 7H-selenopyrano[3,2-f][1]benzothiophene-7-one; 2H-thienol[3,2-g][1]benzopyran-2-one; 7H-thienol[3,2-g][1]benzothiopyran-7-one; 7H-thiopyrano[3,2-f][1]benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'- diethyloxadicarbocyanine; 1,1'-diethylthiacarbocyanine; 3,3'-dialkylthiacarbocyanines (n=2–18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminsterfullerene; [1-methyl-succinate-4-methyl-cyclohexadiene-2,3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl)porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:2'"3'"-q) porphyrazine; zinc (II) 2-(3-pyridyloxy)benzo[b]-10,19,28-tri(1,1-dimethylethyl)trinaphtho[2',3'-g:2"3"1::2'",3'"-q] porphyrazine; zinc (II) 2,18-bis-(3-pyridyloxy)dibenzo[b,1]-10,26-di(1,1-dimethyl-ethyl)dinaphtho[2',3'-g:2'",3'"-q] porphyrazine; zinc (II) 2,9-bis-(3-pyridyloxy)dibenzo[b,g]-17,26-di(1,1-dimethyl-ethyl)dinaphtho[2",3"-1:2'", 3'"-q] porphyrazine; zinc (II) 2,9,16-tris-(3-pyridyloxy)tribenzo[b,g,1]-24=(1,1-dimethyl-ethyl)naphtho[2'", 3'"-q] porphyrazine; zinc (II) 2,3-bis-(3-pyridyloxy)benzo[b]-10,19,28-tri(1,1-dimethyl-ethyl)trinaphtho[2',3'-g:2",3"1:2'", 3'"-q]porphyrazine; zinc (II) 2,3,18,19-tetrakis-(3-pyridyloxy)dibenzo[b,1]-10,26-di(1,1-dimethyl-ethyl) trinaphtho[2', 3'-g:2'",3'"-q]porphyrazine; zinc (II) 2,3,9,10-tetrakis-(3-pyridyloxy) dibenzo[b,g]-17,26-di(1,1-dimethyl-ethyl)dinaphtho[2",3"-1:2'",3'"-q]porphyrazine; zinc (II) 2,3,9,10,16,17-hexakis-(3-pyridyloxy)tribenzo[b,g,1]-24-(1,1-dimethyl-ethyl)naphtho[2'",3'"-q]porphyrazine; zinc (II) 2-(3-N-methyl)pyridyloxy)benzo[b]-10,19,28-tri(1,1-dimethyl-ethyl)trinaphtho[2',3'-g:2",3"1:2'",3'"-q] porphyrazine monoiodide; zinc (II) 2,18-bis-(3-(N-methyl)pyridyloxy)dibenzo[b,1]-10,26-di(1,1-dimethylethyl) dinaphtho[2',3'-g:2'",3'"-q]porphyrazine diiodide; zinc (II) 2,9-bis-(3-(N-methyl)pyridyloxy)dibenzo[b,g]-17,26-di(1,1-dimethylethyl)dinaphtho[2",3"-1:2'",3'"-q]porphyrazine diiodide; zinc (II) 2,9,16-tris-(3-(N-methyl-pyridyloxy) tribenzo[b,g,1]-24-(1,1-dimethylethyl)naphtho[2'",3'"-q] porphyrazine triiodide; zinc (II) 2,3-bis-(3-(N-methyl)pyridyloxy)benzo[b]-10,19,28-tri(1,1-dimethylethyl) trinaphtho[2',3'-g:2",3"-1:2'",3'"-q]porphyrazine diiodide; zinc (II) 2,3,18,19-tetrakis-(3-(N-methyl)pyridyloxy) dibenzo[b,1]-10,26-di(1,1-dimethyl)dinaphtho[2',3'-g:2'", 3'"-q]porphyrazine tetraiodide; zinc (II) 2,3,9,10-tetrakis-(3-(N-methyl)pyridyloxy)dibenzo[g,g]-17,26-di(1,1-dimethylethyl)dinaphtho[2",3"-1:2'",3'"-q]porphyrazine tetraiodide; zinc (II) 2,3,9,10,16,17-hexakis-(3-(N-methyl) pyridyloxy)tribenzo[b,g,1]-24-(1,1-dimethylethyl)naphtho [2'",3'"-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl)porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfo-phthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimidomethyl sulfonate; aluminum phthalocyanine sulfonate; aluminum phthalocyanine trisulfonate; aluminum (II) phthalocyanine trisulfonate; aluminum (II) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylene-thio[(dimethylamino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium (II) phthalocyanine trisulfonate-chloride; gallium (II) phthalocyanine trisulfonate; $GaPcS_1tBu_3$; $GaPcS_2tBu_2$; $GaPcS_3tBu_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3,6-dioxaheptyloxy)phthalocyanine; magnesium t-butyl-phthalocyanine; nickel (II) 2,3,9,10,16,17,23,24-octakis(3,6-dioxaheptyloxy)phthalocyanine; palladium (II) octa-n-butoxy phthalocyanine; palladium (II) tetra(t-butyl)-phthalocyanine; (diol) (t-butyl)$_3$-phthalocyanato palladium (II); ruthenium(II) dipotassium[bis(triphenyl-phosphine-monosulphonate)phthalocyanine; silicon phthalocyanine bis(tri-n-hexyl-siloxy)-; silicon phthalocyanine bis(tri-phenyl-siloxy)-; HOSiPcOSi(CH$_3$)$_2$(CH$_2$)$_3$N(CH$_3$)$_2$; HOSiPcOSi (CH$_3$)$_2$(CH$_2$)$_3$N(CH$_2$CH$_3$)$_2$; SiPc[OSi(CH$_3$)$_2$(CH$_2$)$_3$N(CH$_2$)$_2$]$_2$; SiPc[OSi(CH$_3$)$_2$(CH$_2$)$_3$N(CH$_2$CH$_3$)(CH$_2$)$_2$N(CH$_3$)$_2$]$_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy)phthalocyanine; zinc (II) 2,3,9,10,16,17,23,24-octakis(3,6-dioxaheptyloxy)phthalocyanine; zinc (II) 1,4,8,11,15,18,22,25-octa-n-butoxy-phthalocyanine; zn(II)-phthalocyanine-octabutoxy; zn(II)-phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1,1-dimethyl-2-phthalimido)ethyl phthalocyanine; zinc (II) tetrakis-(1,1-dimethyl-2-amino)-ethyl-phthalocyanine; zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl)pyridyloxy)phthalocyanine tetraiodide; and zinc (II) 2,3,9,10,16,17,23,24-octakis-(3-(N-methyl)pyridyloxy) phthalocyanine complex octaiodide; and zinc (II) 2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 $\mu$M); methylene blue (14 $\mu$M); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum t-butyl-chloronaphthalocyanine; silicon bis (dimethyloctadecylsiloxy) 2,3-naphthalocyanine; silicon bis (dimethyloctadecylsiloxy)naphthalocyanine; silicon bis (dimethylthexylsiloxy) 2,3-naphthalocyanine; silicon bis (dimethylthexylsiloxy)naphthalocyanine; silicon bis(t-butyldimethylsiloxy) 2,3-naphthalocyanine; silicon bis(tert-butyldimethylsiloxy)naphthalocyanine; silicon bis(tri-n-hexylsiloxy) 2,3-naphthalocyanine; silicon bis(tri-n-hexylsiloxy)naphthalocyanine; silicon naphthalocyanine; t-butylnaphthalocyanine; zinc (II) naphthalocyanine; zinc (II) tetraacetyl-amidonaphthalocyanine; zinc (II) tetraaminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a] phenothiazinium, 5-amino-9-diethylamino-; benzo[a] phenothiazinium, 5-amino-9-diethylamino-6-iodo-; benzo [a]phenothiazinium, 5-benzylamino-9-diethylamino-; benzo [a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a] phenoxazinium, 5-amino-9-diethylamino-2,-iodo; benzo[a] phenoxazinium, 5-amino-9-diethylamino-6-iodo-; benzo[a] phenoxazinium, 5-benzylamino-9-diethylamino-(nile blue 2B); 5-ethylamino-9-diethylamino-benzo[a] phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl) propionic acid); carprofen (3-chlorocarbazole); chlorobenoxaprofen; 2,4-dichlorobenoxaprofen; cinoxacin; ciprofloxacin; decarboxyketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol] hypocrellin B; 3,10-bis[4-(2-aminoethyl)morpholine] hypocrellin B; n-butylaminated hypocrellin B; 3,10-bis (butylamine)hypocrellin B; 4,9-bis(butylamine)hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)]hypocrellin B; 5,8-dibromo[1,12-CHBrC(=CH$_2$)CBr(COMe)] hypocrellin B; 5,8-dibromo[1-CH$_2$COMe, 12-COCOCH$_2$Br-]hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH(COCH$_2$I$_2$)-]hypocrellin B; 5,8-diiodo[1,12-CH$_2$C(CH$_2$I)=C(COMe)-] hypocrellin B; 2-(N,N-diethylamino)ethylaminated hypocrellin B; 3,10-bis[2-(N,N-diethylamino)-ethylamine] hypocrellin B; 4,9-bis[2-(N,N-diethyl-amino)-ethylamine] iso-hypocrellin B; dihydro-1,4-thiazine carboxylic acid hypocrellin B; dihydro-1,4-thiazine hypocrellin B; 2-(N,N-dimethylamino)propylamine hypocrellin B; dimethyl-1,3,5, 8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-CH$_2$C(CH$_2$I)=C(COMe)-]hypocrellin B; 8-iodo[1,12-CH$_2$C(CH$_2$I)=C(COMe)-]hypocrellin B; 9-methylamino iso-hypocrellin B; 3,10-bis[2-(N,N-methylamino)propylamine]hypocrellin B; 4,9-bis (methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+ iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacteriomeso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyloxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl) bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl) bis[3,8,12,17-tetramethyl]-; SnCe$_6$-MAb conjugate 1.7:1; SnCe$_6$-MAb conjugate 1.7:1; SnCe6-MAb conjugate 6.8:1; SnCe6-MAb conjugate 11.2:1; SnCe6-MAb conjugate 18.9:1; SnCe$_6$-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy) phthalocyanine; 2,3,9,10,16,17,23, 24-octakis(3,6-dioxaheptyloxy)phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-(2$^3$-carboxy-2$^4$-methoxycarbonyl benzo)-7,12,17-tris(2-methoxyethyl) porphycene; 2-(2-hydroxyethyl)-7,12,17-tri(2-methoxyethyl)porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis (2-methoxyethyl)-9-pelargonyloxy-porphycene; 2,7,12,17-tetrakis(2-methoxyethyl)-9-stearoyloxy-porphycene; 2,7,12, 17-tetrakis(2-methoxyethyl)-9-(N-t-butoxycarbonylglycinoxy)porphycene; 2,7,12,17-tetrakis(2-methoxyethyl)-9-[4-((β-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12, 17-tetrakis(2-methoxyethyl)-9-(glutarimido)-porphycene; 2,7,12,17-tetrakis(2-methoxyethyl)-3-(N,N-dimethylaminomethyl)-porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12, 17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl)porphycene; 2,7, 12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6;13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 $\mu$M); hematoporphyrin (400 $\mu$M); hematoporphyrin (3 $\mu$M); hematoporphyrin (18 $\mu$M); hematoporphyrin (30 $\mu$M); hematoporphyrin (67 $\mu$M); hematoporphyrin (150 $\mu$M); hematoporphyrin IX; hematoporphyrin monomer; hematoporphyrin dimer; hematoporphyrin derivative; hematoporphyrin derivative (6 $\mu$M); hematoporphyrin derivative (200 $\mu$M); hematoporphyrin derivative A (20 $\mu$M); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra(o-hydroxyphenyl)porphyrin; 5,10,15,20-tetra(m-hydroxyphenyl)porphyrin; 5,10,15,20-tetrakis-(m-hydroxyphenyl)porphyrin; 5,10,15,20-tetra(p-hydroxyphenyl)porphyrin; 5,10,15,20-tetrakis (3-methoxyphenyl)porphyrin; 5,10,15,20-tetrakis (3,4-dimethoxyphenyl)porphyrin; 5,10,15,20-tetrakis (3,5-dimethoxyphenyl)porphyrin; 5,10,15,20-tetrakis (3,4,5-trimethoxyphenyl)porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylaminoformamide; protoporphyrin formamide; sapphyrin 1 3,12,13,22-tetraethyl-2,7,18,23 tetramethyl sapphyrin-8,17-dipropanol; sapphyrin 2 3,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl)porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium)porphine; meso-tetra-(4-N,N,N"-trimethylamino-phenyl) porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra(4-sulfonatophenyl)porphine; tetraphenylporphyrin sulfonate; meso-tetra(4-sulfonatophenyl)porphine; tetrakis (4-sulfonatophenyl) porphyrin; meso-tetra(4-sulfonatophenyl)porphine; meso(4-sulfonatophenyl)porphine; meso-tetra(4-sulfonatophenyl) porphine; tetrakis(4-sulfonatophenyl)porphyin; meso-tetra (4-N-trimethylanilinium)-porphine; uroporphyrin; uroporphyrin I (17 $\mu$M); uroporphyrin IX; and uroporphyrin I (18 $\mu$M).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-aminomethylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5',2"-terthiophene-sulphone; 5-bromo-2,2':5',2"-terthiophene; 5-(butynyl-3'"-hydroxy)-2, 2':5',2"-terthiophene; 5-carboxyl-5"-trimethylsilyl-2,2':5', 2"-terthiophene; 5-cyano-2,2':5',2"-terthiophene; 5,5"-dibromo-2,2': 5',2"-terthiophene; 5-(1'",1'"-dibromoethenyl)-2,2':5',2"-terthiophene; 5,5"-dicyano-2, 2':5',2"-terthiophene; 5,5"-diformyl-2,2':5terthiophene; 5-difluoromethyl-2,2':5',2"-terthiophene; 5,5"-diiodo-2,2':5', 2"-terthiophene; 3,3"-dimethyl-2,2':5',2"-terthiophene; 5,5"-dimethyl-2,2':5',2"-terthiophene; 5-(3'",3'"-dimethylacryloyloxymethyl)-2,2':5',2"-terthiophene; 5,5"-di-(t-butyl)-2,2':5',2"-terthiophene; 5,5"-dithiomethyl-2, 2':5',2"-terthiophene; 3'-ethoxy-2,2':5',2"-terthiophene; ethyl 2,2':5',2"-terthiophene-5-carboxylic acid; 5-formyl-2, 2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5', 2terthiophene; 3'-methoxy-2,2':5',2"-terthiophene; 5-methyl-2,2':5',2"-terthiophene; 5-(3'"-methyl-2'"-butenyl)-2,2':5',2"-terthiophene; methyl 2,2':5',2"-terthiophene-5-[3'"-acrylate]; methyl 2,2':5',2"-terthiophene-5-(3'"-propionate); N-allyl-2,2':5',2"-terthiophene-5-sulphonamide; N-benzyl-2,2':5',2"-terthiophene-5-sulphonamide; N-butyl-2,2':5',2"-terthiophene-5-sulphonamide; N,N-diethyl-2,2':5',2"-terthiophene-5-sulphonamide; 3,3',4',3"-tetramethyl-2,2':5', 2"-terthiophene; 5-t-butyl-5"-trimethylsilyl-2,2':5',2"-terthiophene; 3'-thiomethyl-2,2':5',2"-terthiophene; 5-thiomethyl-2,2':5',2"-terthiophene; 5-trimethylsilyl-2, 2':5',2"-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2, 2'-bithiophene derivative; 5-(ethoxybutynyl)-2,2'-bithiophene derivative, and misclaneous thiophenes such as 2,5-diphenylthiophene; 2,5-di(2-thienyl)furan; pyridine, 2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene)bis-; thiophene, 2,2'-(1,4-phenylene)bis-; 2,2':5', 2":5",2'"-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5', 7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4', 5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5', 7'-tetraiodo-fluorescein, dianion); erythrosin; erythrosin dianion; erythrosin B; fluorescein; fluorescein dianion; phloxin B (2',4', 5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammnonium salt; rose bengal benzyl ester, triphenyl pyrilium; rose bengal bis(triethyl-ammonium)salt) (3,4,5,6-tetrachloro-2',4',5',7'-tetraiodofluorescein, bis(triethyl-ammonium salt); rose bengal bis(triethyl-ammonium)salt; rose bengal bis(benzyl-triphenyl-phosphonium) salt (3,4,5,6-tetrachloro-2',4',5',7'-tetraiodofluorescein, bis(benzyl-triphenyl-phosphonium) salt); rose bengal bis(diphenyl-iodonium)salt (3,4,5,6-tetrachloro-2',4',5',7'-tetraiodofluorescein, bis(diphenyl-iodonium)salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

Particularly preferred PSs are the green porphyrins, such as BPD-DA, -DB, -MA, and -MB, and in particular BPD-MA, EA6, and B3. These compounds are porphyrin derivatives obtained by reacting a porphyrin nucleus with an alkyne in a Diels-Alder type reaction to obtain a monohydrobenzoporphyrin, and they are described in detail in the issued U.S. Pat. No. 5,171,749, which is hereby incorporated in its entirety by reference. Of course, combinations of photosensitizers may also be used. It is preferred that the. absorption spectrum of the photosensitizer be in the visible range, typically between 350 nm and 1200 nm, more preferably between 400–900 nm, and even more preferably between 600–900 nm.

BPD-MA is described, for example, in U.S. Pat. No. 5,171,749; EA6 (also known as QLT 0074) and B3 are described in U.S. Pat. No. 5,929,105 and 5,990,149, respectively, all of which are incorporated herein by reference. Preferred green porphyrins for the practice of the invention have the following basic structure:

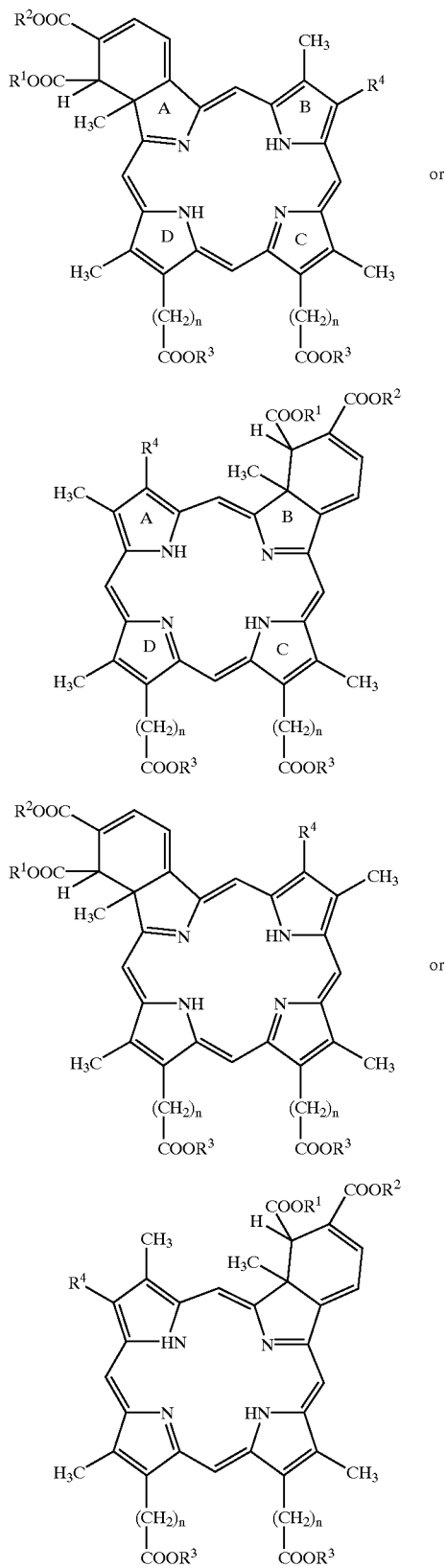

where $R^4$ is vinyl or 1-hydroxyethyl and $R^1$, $R^2$, and $R^3$ are H or alkyl or substituted alkyl.

BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MA$_C$ and BPD-MA$_D$, which are the components of Verteporfin, as well as illustrations of A and B ring forms of EA6 and B3, are as follows:

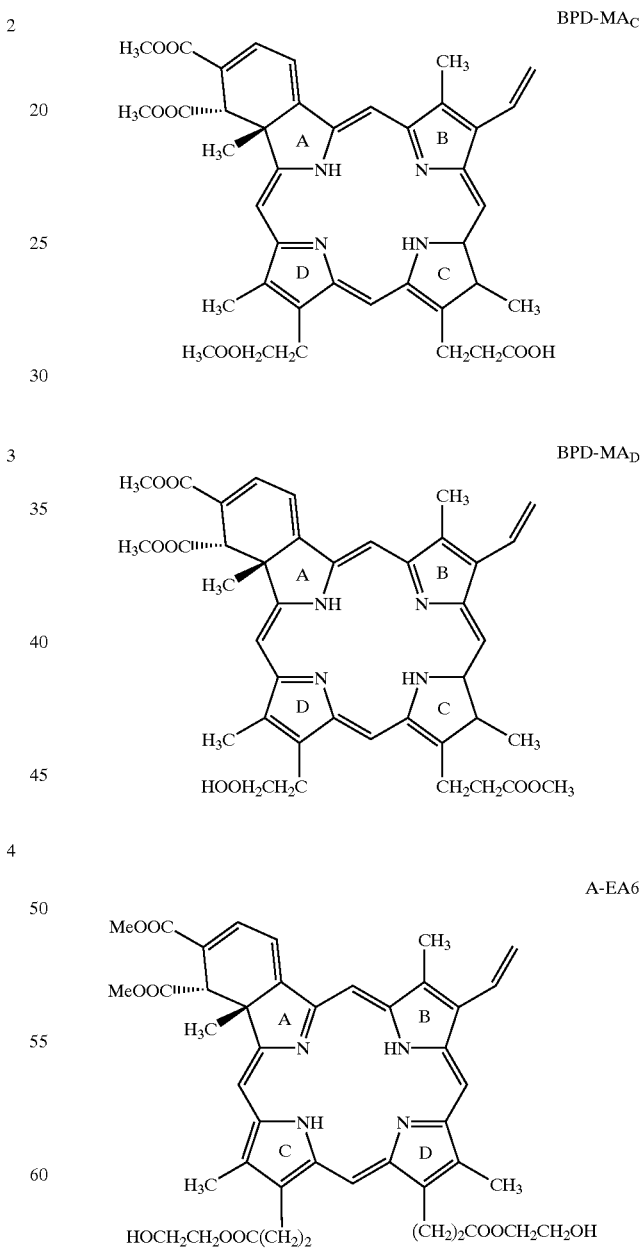

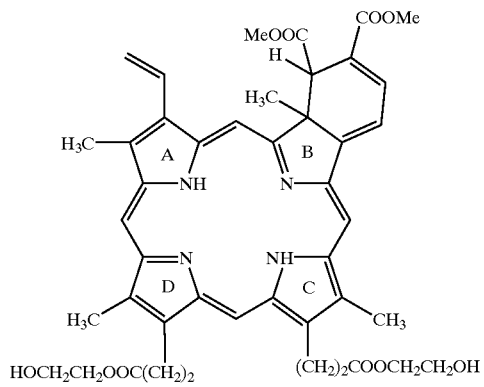

B-EA6

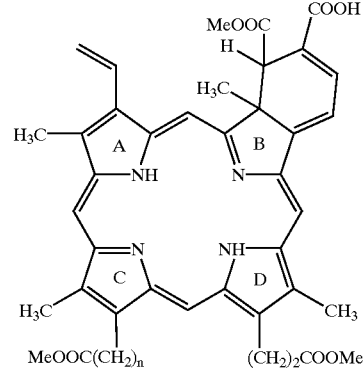

A-B3

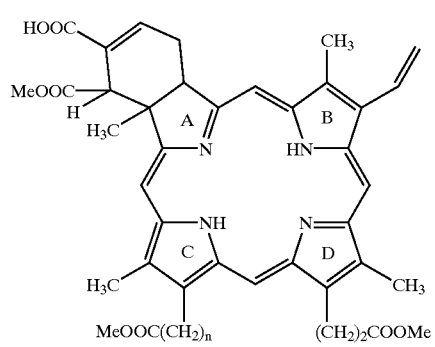

Related compounds of formulas 3 and 4 are also useful; in general, $R^4$ will be vinyl or 1-hydroxyethyl and $R^1$, $R^2$, and $R^3$ are H or alkyl or substituted alkyl.

Additional examples of hydrophobic BPD B-ring compounds that are difficult to formulate, and are especially well suited to use in the invention are shown below, where the asterisks indicate chiral carbon positions.

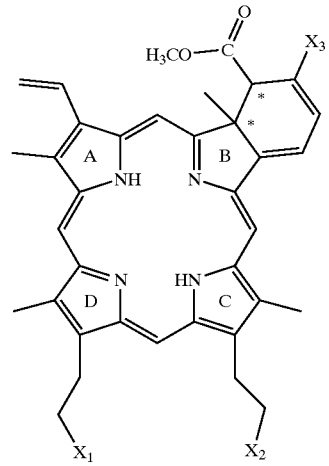

| Drug | X1 | X2 | X3 |
|---|---|---|---|
| QLT0060 | $CO(O(CH_2)_2)OH$ | $CO(O(CH_2)_2)OH$ | $COOCH_3$ |
| QLT0069 | $COOCH_3$ | $COOCH_3$ | $COOH$ |
| QLT0078 | $CO(O(CH_2)_2)_2OH$ | $CO(O(CH_2)_2)_2OH$ | $COOCH_3$ |
| QLT0080 | $CO(O(CH_2)_2)_3OH$ | $CO(O(CH_2)_2)_3OH$ | $COOCH_3$ |
| QLT0081 | $CO(O(CH_2)_2)_2OCH_3$ | $CO(O(CH_2)_2)_2OCH_3$ | $CO(O(CH_2)_2)_2OCH_3$ |
| QLT0082 | $CO(O(CH_2)_2)_2OH$ | $CO(O(CH_2)_2)_2OH$ | $CO(O(CH_2)_2)_2OH$ |
| QLT0083 | $CO(O(CH_2)_2)_3OH$ | $CO(O(CH_2)_2)_3OH$ | $CO(O(CH_2)_2)_3OH$ |
| QLT0087 | $CO(O(CH_2)_2)_4OH$ | $CO(O(CH_2)_2)_4OH$ | $COOCH_3$ |
| QLT0088 | $COOCH_3$ | $COOCH_3$ | $CONH(C_6H_4)(C_5H_{10}N)$ |
| QLT0090 | $CO(O(CH_2)_2)_5OH$ | $CO(O(CH_2)_2)_5OH$ | $COOCH_3$ |
| QLT0093 | $CO(O(CH_2)_2)_5OH$ | $CO(O(CH_2)_2)_5OH$ | $CO(O(CH_2)_2)_5OH$ |

Additionally, the photosensitizers used in the invention may be conjugated to various ligands to facilitate targeting to the target tissue. These ligands include those that are receptor-specific as well as immunoglobulins and fragments thereof. Preferred ligands include antibodies in general and monoclonal antibodies, as well as immunologically reactive fragments of both.

It is well known in the art that for PDT using any particular PS, the total PDT outcome depends in part on the balance of three parameters that can be varied: the concentration of PS, the light intensity (also referred to as power or fluence rate, usually expressed as mW/cm² of target tissue), and the duration of irradiation. The latter two parameters, time and light intensity determine the total fluence (also referred to as total light dose, or irradiance), which is usually expressed as J/cm2 of target tissue. Another variable that must be taken into consideration is the time gap between administration of the PS, and the application of light to the target tissue. The rate of uptake into the target tissue and the rate of clearance or elimination of a particular PS determines the amount of PS available for activation in the target tissue at any particular time after PS administration. Ideally, light is administered when an effective amount of PS (an amount sufficient to provide an efficacious effect in the PDT being administered) has accumulated in the target tissue, but before a significant amount of PS has accumulated in non-target tissues. An effective or sufficient amount of light is that which provides an efficacious effect in the PDT being administered. This time period has generally been determined to be between 1 minute and 3 hours (see U.S. Pat. Nos. 5,705,518 and 5,770,619 which are incorporated by reference as if fully set forth). However, more precise timing can be determined by pharmacokinetic studies comparing the presence of PS in target and not-target tissues at various time points after PS administration.

It is understood that the selection of particular fluence rates will vary according to the nature of the macula, the DME lesion, or lesion resulting in macular edema being treated and the nature of the PS employed. However, the conditions for PDT (including PS concentration, fluence rate, and time of irradiation) cannot vary over any arbitrary range. There are actual constraints which are known by the skilled practitioner with the use of any PS in PDT. Preferred rates for use with green porphyrins or BPDs is from about 100 to 250, about 250 to 300, about 300 to 350, about 350 to 400, about 400 to 450, about 450 to 500, and about 500 to 550, about 550 to 600, about 600 to 650, about 650 to 700, about 700 to 750, about 750 to 800, about 800 to 850 and about 850 to 900 mW/cm². Particularly preferred is a fluence rate in the range of 200 to 600 mW/cm².

As indicated above, the total PDT dose depends on the balance of at least the concentration of PS employed, light intensity (fluence rate), and time of irradiation which determines total energy. The values set forth hereinbelow for these parameters indicates the range in which they may be varied; however, equivalents of the following are known to the skilled practitioner and are also within the scope of the invention.

The PS concentration in the formulation to be administered will depend on the nature of the lesion to be treated, the manner in which the formulation is administered, and the nature of the PS. However, these values are merely suggestions and may not apply to all PSs. For localized application of BPD-MA and other green porphyrins or porphyrin derivatives (especially those listed above), a range of about 0.01 to about 0.2 or about 0.5 mg/ml in the PS formulation to be applied is contemplated. Preferably, about 0.075 mg/ml is used. For systemic application of PS, the range may be about 2–8 (or more preferably about 6) mg/m² (BPD-MA/body surface area). About 6 mg/m² is approximately 0.15 mg/kg for a human patient, but will vary depending on the height and weight of a particular patient.

Systemic administration can also be stated in terms of amount of PS to body weight of the subject being treated. Dosages for this invention stated in such terms are less than about 10 $\mu$g/kg to 100 mg/kg body weight, preferably less than about 10 mg/kg, less than about 5 mg/kg, less than about 2 mg/kg, less than about 1 mg/kg, less than about 0.5 mg/kg, less than about 0.25 mg/kg, less than about 0.15 mg/kg, less than about 0.1 mg/kg, or less than about 0.05 mg/kg. One preferred concentration is about 0.15 mg/kg in humans. Preferably, the PS is infused into a subject over a short period, such as, but not limited to, about 5 to about 120 minutes, about 10 to about 90 minutes, about 20 to about 60 minutes, or about 30 to 45 minutes. Particularly preferred is an infusion over 10, but less than about 120, minutes.

The PS/photoactive agent is preferably formulated so as to provide an effective concentration to the target ocular tissue. The photoactive agent may be coupled to a specific binding ligand which may bind to a specific surface component of the target ocular tissue or, if desired, by formulation with a carrier that delivers higher concentrations to the target tissue. The formulation may be a liposomal formulation, an emulsion, or simply an aqueous solution, depending on the PS being used, and whether it is hydrophobic or hydrophilic. Buffers and other excipients may also be added. Gelling agents and other excipients may also be employed.

The nature of the formulation will depend in part on the mode of administration and on the nature of the photoactive agent selected. Any pharmaceutically acceptable excipient, or combination thereof, appropriate to the particular photoactive compound may be used. Thus, the photoactive compound may be administered as an aqueous composition, as a transmucosal or transdermal composition, or in an oral formulation. Liposomal or lipid-based compositions are particularly preferred especially where the photoactive agent is a green porphyrin. Such formulations are believed to deliver the green porphyrin selectively to the low-density lipoprotein component of plasma which, in turn acts as a carrier to deliver the active ingredient more effectively to the desired site.

The optimum time following PS administration until light treatment can also vary widely depending on the mode of administration, the form of administration and the specific ocular tissue being targeted. Typical times after administration of the photoactive agent range from about 1 minute to about 48 hours, preferably about 1 minute to 3 hours, about 5–30 minutes, and more preferably about 10–25 minutes. Particularly preferred is irradiation at about 15 minutes after the start of a ten minute infusion when BPD-MA is used as the PS. The incubation before irradiation may occur in the dark or low-level light may be supplied during PS administration.

The irradiation levels (total light dose) will be in the range generally employed for PDT treatment known in the art. Typical levels for the practice of the invention are in the range of about 1, about 5, about 12.5, about 25, about 50, about 75, about 100, about 125, about 150, about 175 and about 200 J/cm$^2$. Especially preferred are levels in the range of about 1 to about 50 J/cm$^2$ and about 5 to about 30 J/cm$^2$. Preferred are fluence rates of about 300 mW/cm$^2$ used to deliver about 25 J/cm$^2$ in about 83 seconds, about 12.5 mW/cm$^2$ in about 42 seconds, and about 50 mW/cm$^2$ in about 166 seconds, or fluence rates of about 600 mW/cm$^2$ used to deliver about 12.5 mW/cm$^2$ in about 21 seconds, 25 mW/cm$^2$ in about 42 seconds, or 50 mW/cm$^2$ in about 83 seconds. The radiation can be supplied by any convenient source using a wavelength absorbed by the PS used. Examples of sources for use in the present methods include any assembly capable of producing visible light. Particularly preferred is light from a diode laser delivered via a fiber optic via a slit lamp and utilizing a suitable contact lens that is placed on the eye of the subject.

PS spectra, as well as wavelengths for PS activation, have been described in the art. Irradiation of the administered PS is at a wavelength absorbed by the PS selected. For any particular PS, it is a trivial matter to ascertain the spectrum. For green porphyrins, however, the desired wavelength range is generally between about 550 and 695 nm. Preferred wavelengths for the practice of the invention are at about 685–695 nm, particularly at about 686, about 687, about 688, about 689, about 690, about 691, and about 692 nm.

The area of the eye that is exposed to light depends on the nature and extent of the lesion(s) that have been detected by angiography. For focal lesions, a spot size is chosen that generally encompasses the lesion. For diffuse lesions, a spot size that encompasses the area in which leakage has been detected can be treated, and will generally be larger than the spot size used in the treatment of focal lesions. Spot sizes can range anywhere from 100 to 8000 microns or more in diameter, depending on the size of the lesion to be treated, and the maximum spot diameter that can be produced by the apparatus being used. Multiple areas of leakage can be treated by repeating the irradiation step on two or more areas in which diffuse leakage has been detected. If this is done, the subsequent areas are preferably be treated immediately after the first area has been treated. Irradiation spots are generally round, due to the fact that most types of apparatus produce a circular spot, but the spot irradiated need not be circular.

Another approach to providing light to diffuse lesions is to irradiate multiple small spots arranged in a "grid" pattern. The spot sizes are in the range of about 25 to about 500 microns in diameter, most preferably in the range of about 50 to about 200 microns in diameter. Preferably, there is a distance of about 0.5 to about 2.0 spot diameters between individual spots, most preferably about 1.0 spot diameters. The grid pattern of irradiation is preferably performed over an area sufficient to cover areas of diffuse leakage.

While the above presents the use of light containing an activating wavelength, any form of appropriately activating electromagnetic radiation, such as from ultraviolet to visible and infra red light, may be used to activate a photosensitizer as used in the present invention. This is obviously of particular relevance to photosensitizers with an activation wavelength above or below the range of visible light. It should also again be pointed out that because there are three significant factors—the concentration of the photosensitizing drug, the intensity of the radiation employed and the time of exposure to light, which determines the total amount of energy ultimately delivered to the target tissue, an increase in one or more of these factors generally permits a decrease in the remaining factors.

For example, if it is desired to irradiate only for a short period of time the energy of irradiation or the concentration of the drug may be increased. Conversely, if longer time periods of irradiation are permitted, lower irradiation intensities and lower drug concentrations are desirable. It is understood that the manipulation of these parameters will vary according to the nature of the lesion and tissue being treated and the nature of the photosensitizer (PS) employed. One rough means for comparing different PDT protocols is the product of PS concentration (e.g., in ng/ml)×intensity (e.g., in mW/cm$^2$)×time (e.g., in seconds). However, it is difficult to set absolute numbers for this product since there are constraints on each of the parameters individually. For example, if the intensity is too low, the PS will not be activated consistently; if the intensity is too high, hyperthermic and other damaging effects may occur. Additionally, in some instances with some photosensitizers and the concentration used, ambient or environmental light available at the target cell or tissue undergoing PDT may be sufficient in the absence of additional deliberate irradiation.

Similarly, PS concentrations cannot vary over any arbitrary range. There may also be constraints on the time during which radiation can be administered. Accordingly, the product of the foregoing equation is only a rough measure. However, this approach may provide a convenient index that can be adjusted according to the relative potency of the PS employed, and in general, an increase in intensity would permit a decrease in time of irradiation, and so forth.

Treatments in accordance with the present invention may also be repeated one or more times, as for example, if the skilled practitioner finds a recurrence of the lesion. Repeat treatments are preferably at intervals of about 1, about 2 and about 3 months, with a minimum of 1, 2, 3 or 4 repeats.

Treatment efficacy can be evaluated by a number of different protocols, including, but not limited to fluorescein or indocyanine green angiography to determine the area of leakage from the lesion before and after treatment. Angiography using the aforementioned dyes is well known in the art.

Of particular importance with respect to the present invention is the evaluation of visual acuity and vision loss. The former is done using means standard in the art and conventional "eye charts" in which visual acuity is evaluated by the ability to discern letters of a certain size, usually with five letters on a line of given size. Preferably, the eye chart is an "ETDRS" eye chart described in publications related to the EDTRS study, or in Murphy, R. P. in *Current Techniques* in *Opthalmic Laser Surgery*, 3rd Edition, Edited by L. J. Singerman and G. Cascas, Butterworth Heinemann, 2000 Measures of visual acuity are known in the art and standard means are used to evaluate visual acuity according to the present invention.

In macular edemas involving leakage (or hemorrhage) from vasculature, the reabsorption of the leakage/hemorrhage after an acute phase or treatment according to the present invention may be followed by identification and/or evaluation of macromolecular and/or molecular vascular characteristics that are of prognostic significance. In a preferred embodiment when macular edema associated with CRVO or BRVO is treated according to the present invention, the retinal vascular (vein) characteristics with a prognostic significance may be identified and evaluated after reabsorption of the leakage/hemorrhage. Similarly, the vascular characteristics associated with DME may be evaluated as well.

Having now generally described the invention, the same will be more readily understood through reference to the following examples which are provided by way of illustration, and are not intended to be limiting of the present invention, unless specified.

EXAMPLE 1

Treatment of DME with PDT

Patients having type I or type II diabetes mellitus are examined for the presence of lesions in the eye indicative of DME with diffuse lesions. Macular/retina edema is detected by slit lamp biomicroscopy, which detects retinal thickening. Patients are evaluated by fluorescein angiography within 7 days of treatment to determine the area of leakage in the macular/retina area. Patients are chosen who have evidence of diffuse macular/retina edema with fluorescein angiography leaking within 300–500 micrometers of the central area. Those determined as qualified for treatment of DME are divided into 6 groups. Groups A, B and C are treated with a regimen in which they are administered 6 mg/M$^2$ (of body surface area) with Verteporfin for Injection (Visudyn™, Novartis Ophthalmics) in a 5% dextrose solution in a total volume of 30 ml. Administration is by intravenous infusion over a period of 10 minutes. Groups D, E and F are administered 30 ml of a 5% dextrose solution (placebo) using the same procedure. Fifteen minutes after the end of the infusion, laser irradiation to the lesion is performed using laser light of 689+/−3 nm, delivered via a fiber optic via a slit lamp and utilizing a suitable contact lens. An ophthalmic diode laser system (Coherent Ocular Photoactivation Diode Laser and LaserLink® Coherent Medical Laser, Palo Alto, Calif.) is used. Laser light is delivered at an irradiance of 600 mW/cm$^2$. A circular spot of approximately 6000 microns encompassing the area of diffuse leakage is exposed to laser light using the apparatus described above. Groups A and D receive a total fluence of 12.5 J/cm$^2$. Groups B and E receive a total fluence of 25 J/cm$^2$. Groups C and E receive a total fluence of 50 J/cm$^2$. Evaluation by fluorescein angiography is carried out at 1 and 4 weeks after treatment. Patients are also assessed for visual acuity at 1 and 4 weeks after treatment.

EXAMPLE 2

Treatment of DME Using a Photic Injury Model in the Monkey

The following model can be used to determine the effective dosages of a particular photosensitive compounds by replacing verteporfin with the test compound in the protocol. The model is a photic injury model in the rhesus monkey. The pupils of the monkey eye are dilated with 10% phenylephrine hydrochloride and 1% atropine (two drops per eye). An indirect ophthalmoscope (American Optical), set at 7.5 volts with a General Electric 1460 bulb, is placed 10 inches from a 20 diopter-condensing lens situated 2¼ inches from the cornea. The light is focused on the posterior pole of the retina. The beam power is 0.11 watts, measured by a radiometer at the cornea, and is calculated to give a retinal intensity of about 200 mW/cm$^2$. The retina is then exposed to the light for 1½ hours (Tso et al. 1983 Ophthalmology 90: 952–963). Twenty-four hours after photic-injury induction, verteporfin is infused intravenously for 10 minutes at a dose varying between 0.1 and 0.5 mg/kg. Fifteen minutes to 3 hours after the start of verteporfin infusion, the retinal lesion area is irradiated with between 1 and 50 J/cm$^2$ 689 nm red light (Coherent OPADL laser). The fluence rate may vary between 100 to 600 mW/cm$^2$. The laser light is applied on the retina through a Mainster Wide-Field lens producing a 5-mm spot that is centered on the photic-injury area to be treated. The retinal edema is evaluated by the ophthalmoscopy, fundus photography, and retinal thickness analyzer (RTA) in vivo between the retinal photic injury and the PDT treatment, as well as before the animals are sacrificed at 24 h, 48 h, 7 days, and 14 days after the low-dose PDT treatment. The eyes are enucleated and the cornea, lens, and vitreous are removed. A circle of the examined tissue with an 8-mm diameter, including the PDT treated area (d=5 mm) plus the adjacent untreated area is delineated by sharp cuts. The tissue is placed in OCT freezing compound and frozen in 2-methylbutane cooled with liquid nitrogen. Serial cross sections (6–8 m) are cut from each specimen, fixed in 4% PFA for 15 min, and then stained with hematoxylin and eosin for the histology study and the retinal edema thickness measurement.

EXAMPLE 3

Treatment of DME in a Rat Model With Verteporfin

The following model can be used to determine the effective dosages for conducting PDT with photosensitive compounds other than verteporfin by substituting the compound to be tested in the protocol. The model is a Streptozotocin-induced diabetes model in the rat. Long-Evans rats weighing approximately 200 g receive a single 60 mg/kg injection of Streptozotocin (Sigma) in 10 mM citrate buffer (pH 4.5) after an overnight fast. Animals with blood glucose levels greater than 250 mg/dl 24 h later are considered diabetic. Blood pressure is measured by using a noninvasive cuff sensor and monitoring system (Ueda Electronics, Tokyo). Blood treated with the anticoagulant EDTA is drawn from the abdominal aorta of each animal after the experiment. The blood sample is analyzed with a hematology analyzer (Miyamoto K, et al. 1999 Proc. Natl. Acad. Sci USA: 96: 10836–41.)

Seven days after the development of diabetes, verteporfin is infused intravenously at a dose varying between 0.5 and 2 mg/kg intravenously. Fifteen minutes to 3 hours after drug administration, 1 to 50 J/cm$^2$ of 689 nm light with a fluence rate from 100 to 600 mW/cm$^2$ is applied through a coverslice on a 3.5-mm laser spot on the posterior pole area including the macula. The retinopathy is evaluated by ophthalmoscopy, fundus photography, and retinal thickness analyzer (RTA). The integrity of the blood-retinal barriers is assessed by vitreous fluorophotometry and quantitative fluorescence microscopy (Jonasson O. et al Ann. Surg. 1985 201: 27–38; Docarmo A., et al. 1998 Exp Eye Res 67 :569–75; Van Schaik H. J. et al. 1998 Int Ophthalmol 22: 97–104) before PDT, as well as before the animals are sacrificed at 24 h, 48 h, 7 days, and 14 days after PDT. The eyes are enucleated and the cornea, lens, and vitreous are removed. A circle of the examined tissue with a 4.5-mm diameter, including the PDT treated area (d=3.5 mm) plus the adjacent light-untreated area are delineated by sharp cuts. The tissue is placed in OCT freezing compound and frozen in 2-methylbutane cooled with liquid nitrogen. Serial cross sections (5 m) are cut from each specimen, fixed in 4% PFA for 15 min, and then stained with hematoxylin and eosin for histopathological evaluation of diabetic retinopathy. Sections also are immunostained with the inflammatory cell makers CD4, CD8, MHC-II, and ICAM-1 and the endothelial cell marker CD31 antibodies to quantify the amount of extravasated leukocytes and new capillaries. Cells positive for the previous markers are counted using ImagePro imaging software.

EXAMPLE 4

Treatment of DME in a Talc Retinopathy Monkey Model

The following model can be used to determine the efficacy and dosaging requirements for conducting PDT with photosensitive compounds other than verteporfin by substituting the compound to be tested in the protocol. The model is a talc retinopathy model in the rhesus monkey. The animals are injected intravenously with 0.1 to 0.5 g of talc in a saline suspension twice a week for a period of four months (Kaga N. et al. 1982 Arch Ophthalmol 100: 1644–8.)

Four months after talc injection, when the Brain-Retina-Barrier breaking occurs, verteporfin is infused intravenously for 10 minutes at a dose varying between 0.1 and 0.5 mg/kg. Fifteen minutes to 3 hours after the start of the verteporfin infusion, 1 to 50 J/cm$^2$ 689-nm red light (Coherent OPAL laser) is applied on a 5-mm disc on the macula through a Mainster Wide-Field lens. The fluence rate may vary between 100 to 600 mW/cm$^2$. The animals are followed up by the ophthalmoscopy, fundus photography, fluorescein angiography, and retinal thickness analyzer (RTA) in vivo, between the start of BRB breaking occurrence and the PDT treatment, as well as before the animals are sacrificed at 24 h, 48 h, 7 days, and 14 days after the low-dose PDT treatment. The eyes are enucleated and the cornea, lens, and vitreous are removed. A circle of the examined tissue with a 8-mm diameter, including the PDT treated area (d=5 mm) plus the adjacent light-untreated area is delineated by sharp cuts. The tissue is placed in OCT freezing compound and frozen in 2-methylbutane cooled with liquid nitrogen. Serial cross sections (6–8 m) are cut from each specimen, fixed in 4% PFA for 15 min, and then stained with hematoxylin and eosin for the histology examination.

EXAMPLE 5

Treatment of CRVO or BRVO Associated Macular Edema With PDT

Patients having macular edema due to CRVO or BRVO, acute or thereafter, are identified, and macular edema is detected by slit lamp biomicroscopy. Patients are chosen who have evidence of localized or diffuse macular edema within about 300–500 micrometers of the central area. Those determined as qualified for treatment are administered about 6 mg/M$^2$ (of body surface area) with Verteporfin for Injection (Visudyne™, Novartis Ophthalmics) in a 5% dextrose solution in a total volume of 30 ml. Administration is by intravenous infusion over a period of 10 minutes. Control patients are administered 30 ml of a 5% dextrose solution (placebo) using the same procedure. Fifteen minutes after the end of the infusion, laser irradiation to the lesion is performed using laser light of 689+/−3 nm, delivered via a fiber optic via a slit lamp and utilizing a suitable contact lens. An ophthalmic diode laser system (Coherent Ocular Photoactivation Diode Laser and LaserLink® Coherent Medical Laser, Palo Alto, Calif.) is used. Laser light is delivered at an irradiance of about 600 mW/cm$^2$. A circular spot of approximately 6000 microns encompassing the area of macula edema is exposed to laser light using the apparatus described above. Patients may receive a total fluence of about 12.5 J/cm$^2$, about 25 J/cm$^2$, or about 50 J/cm$^2$. Evaluation by fluorescein angiography is carried out at about 1 and 4 weeks after treatment. Patients are also assessed for visual acuity at about 1 and 4 weeks after treatment. Comparisons may be made against the patients' conditions before treatment or against control patients.

All references cited herein are hereby incorporated by reference in their entireties, whether previously specifically incorporated or not. As used herein, the terms "a", an and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. A method to treat a subject afflicted with diabetic macular edema (DME), macular edema resulting from central retinal vein occlusion (CRVO) or branch retinal vein occlusion (BRVO), said method comprising administering an effective amount of a photosensitizer (PS) to said subject, and irradiating said subject's macula with light having a wavelength absorbed by said PS.

2. The method of claim 1 wherein said subject is afflicted with DME.

3. The method of claim 1 wherein said subject is afflicted with CRVO.

4. The method of claim 1 wherein said subject is afflicted with BRVO.

5. The method of claim 2 wherein said lesion is focal in nature.

6. The method of claim 2 wherein the lesion is diffuse in nature.

7. The method of claim 1 wherein the photosensitizer is a green porphyrin.

8. The method of claim 7 wherein the photosensitizer is verteporfin.

9. The method of claim 1 wherein the light is administered from a laser.

10. The method of claim 9, wherein the light is administered at a dosage of between about 1 and about 50 $J/cm^2$.

11. The method of claim 10 wherein the light is administered at a dosage in the range of about 5 to about 30 $J/cm^2$.

12. The method of claim 1 wherein visual acuity of the subject is improved.

13. The method of claim 1 wherein said subject is human.

14. The method of claim 1 wherein both eyes of said subject are irradiated.

15. A method to reduce the volume of interstitial fluid in the eye of a subject having macular edema selected from diabetic macular edema (DME) and macular edema resulting from central retinal vein occlusion (CRVO) or branch retinal vein occlusion (BRVO), said method comprising administering to the subject an effective amount of a photosensitizer (PS) to said subject, irradiating the macula of said subject with light having a wavelength absorbed by said PS.

16. A method to reduce the leakage of exudate from a lesion in the eye of a subject having diabetic macular edema (DME) and identified as having a lesion, said method comprising administering to the subject an amount of a photosensitizer (PS) sufficient to allow said photosensitizer to localize in said lesion, permitting sufficient time to elapse to allow said PS to localize in said lesion, and irradiating said lesion with light having a wavelength absorbed by said PS.

17. The method of claim 16 wherein said subject has been diagnosed with DME.

18. The method of claim 16 wherein said lesion is focal in nature.

19. The method of claim 16 wherein the lesion is diffuse in nature.

20. The method of claim 15 wherein said subject has been diagnosed with DME, CRVO or BRVO.

21. The method of claim 20 wherein said subject has been diagnosed with DME.

22. The method of claim 20 wherein said subject has been diagnosed with CRVO.

23. The method of claim 20 wherein said subject has been diagnosed with BRVO.

24. The method of claim 15 wherein said subject is human.

25. The method of claim 15 wherein both eyes of said subject are irradiated.

26. The method of claim 15 wherein the photosensitizer is a green porphyrin.

27. The method of claim 26 wherein the photosensitizer is verteporfin.

28. The method of claim 15 wherein the light is administered from a laser.

29. The method of claim 28, wherein the light is administered at a dosage of between about 1 and about 50 $J/cm^2$.

30. The method of claim 29 wherein the light is administered at a dosage in the range of about 5 to about 30 $J/cm^2$.

31. The method of claim 15 wherein visual acuity of the subject is improved.

* * * * *